(12) United States Patent
Pregent, Jr.

(10) Patent No.: US 6,531,696 B2
(45) Date of Patent: Mar. 11, 2003

(54) SYSTEMS AND METHOD FOR DETERMINING SOURCE OF ABRASION IN FILM EQUIPMENT

(76) Inventor: John T. Pregent, Jr., 196 Kenwood Ave., Delmar, NY (US) 12054

( * ) Notice: Subject to any disclaimer, the term of this patent is extended or adjusted under 35 U.S.C. 154(b) by 204 days.

(21) Appl. No.: 09/764,607

(22) Filed: Jan. 17, 2001

(65) Prior Publication Data

US 2002/0092981 A1 Jul. 18, 2002

(51) Int. Cl.$^7$ .............................. G03B 21/42; G01J 1/58
(52) U.S. Cl. ...................... 250/302; 352/56; 352/233; 352/238
(58) Field of Search ........................... 250/302; 352/56, 352/233, 238

(56) References Cited

U.S. PATENT DOCUMENTS

| | | | |
|---|---|---|---|
| 2,606,409 A | | 8/1952 | Gordon |
| 2,608,127 A | * | 8/1952 | Redfield ..................... 352/238 |
| 3,995,157 A | * | 11/1976 | Holub et al. ................ 250/302 |

* cited by examiner

*Primary Examiner*—Jack Berman
(74) *Attorney, Agent, or Firm*—Hoffman, Warnick & D'Alessandro LLC; Spencer K. Warnick

(57) ABSTRACT

Systems and method for determining a source of abrasion in film equipment by using a test film having fluorescent material thereon and illuminating the film equipment using a fluorescence creating light source to cause fluorescence of any part having fluorescent material deposited thereon by the test film.

21 Claims, 2 Drawing Sheets

SYSTEMS AND METHOD FOR DETERMINING SOURCE OF ABRASION IN FILM EQUIPMENT

BACKGROUND OF THE INVENTION

1. Technical Field

The present invention relates generally to film equipment and, more particularly, to a systems and method for determining a source of abrasion in film equipment.

2. Related Art

Providing unhindered and non-abrasive progress of film through film equipment is necessary for proper operation of any film equipment. One exemplary setting where non-abrasive film equipment is necessary are motion picture theaters because theaters require film equipment to operate without interruption to make a profit. Film equipment that is worn to the point where the equipment can cause abrasion to film as it passes therethrough can be expensive in terms of repairing the film and lost revenue from disgruntled patrons of interrupted movie shows.

Abrasion of film through equipment can be caused by a number of structures in the film equipment including, inter alia, rollers, sprockets, gates, shoe assemblies, sound heads, platters, payouts, guards, rails and guide pins. This abrasion can cause a variety damage to film such as binding, abrasion, scratching, tearing, etc. Unfortunately, the source of abrasion is difficult to detect because it is frequently indiscernible to the naked eye. Taking remedial action by a trial-and-error approach is time consuming, expensive and inaccurate. In addition, extensive equipment testing and replacement of equipment is not always an option because of expense. Accordingly, there is a long felt need in the art for a system and method for determining a source of abrasion in film equipment that is easy, inexpensive and accurate.

SUMMARY OF THE INVENTION

In a first aspect of the invention is provided a method for determining a source of abrasion in film equipment, the method comprising the steps of: providing a test film having a fluorescent material thereon; contacting the test film with at least part of the film equipment; and illuminating at least part of the film equipment with a fluorescence creating light source to fluoresce areas on the film equipment upon which the fluorescent material has been deposited.

In a second aspect of the invention is provided a system for determining points of abrasion in film equipment, the system comprising: a test film having a fluorescent material on an exterior surface thereof; and a fluorescence creating light source for illuminating at least a part of the film equipment subsequent to the test film having been contacted thereto, to determine points of abrasion in the film equipment by fluorescing areas upon which the fluorescent material has been deposited.

In a third aspect of the invention is provided a system for determining points of abrasion in film equipment, the system comprising: a section of film for contacting at least a part of the film equipment; a source of fluorescent material for application to the section of film to create a test film; and a fluorescence creating light source for fluorescing any part of the film equipment having fluorescent material deposited thereon from the test film having contacted the part.

The above-described aspects provide systems and method for determining a source of abrasion in film equipment that are easy to use, inexpensive and accurate.

The foregoing and other features and advantages of the invention will be apparent from the following more particular description of preferred embodiments of the invention.

BRIEF DESCRIPTION OF THE DRAWINGS

The preferred embodiments of this invention will be described in detail, with reference to the following figures, wherein like designations denote like elements, and wherein.

DESCRIPTION OF THE PREFERRED EMBODIMENTS

Figure 1:
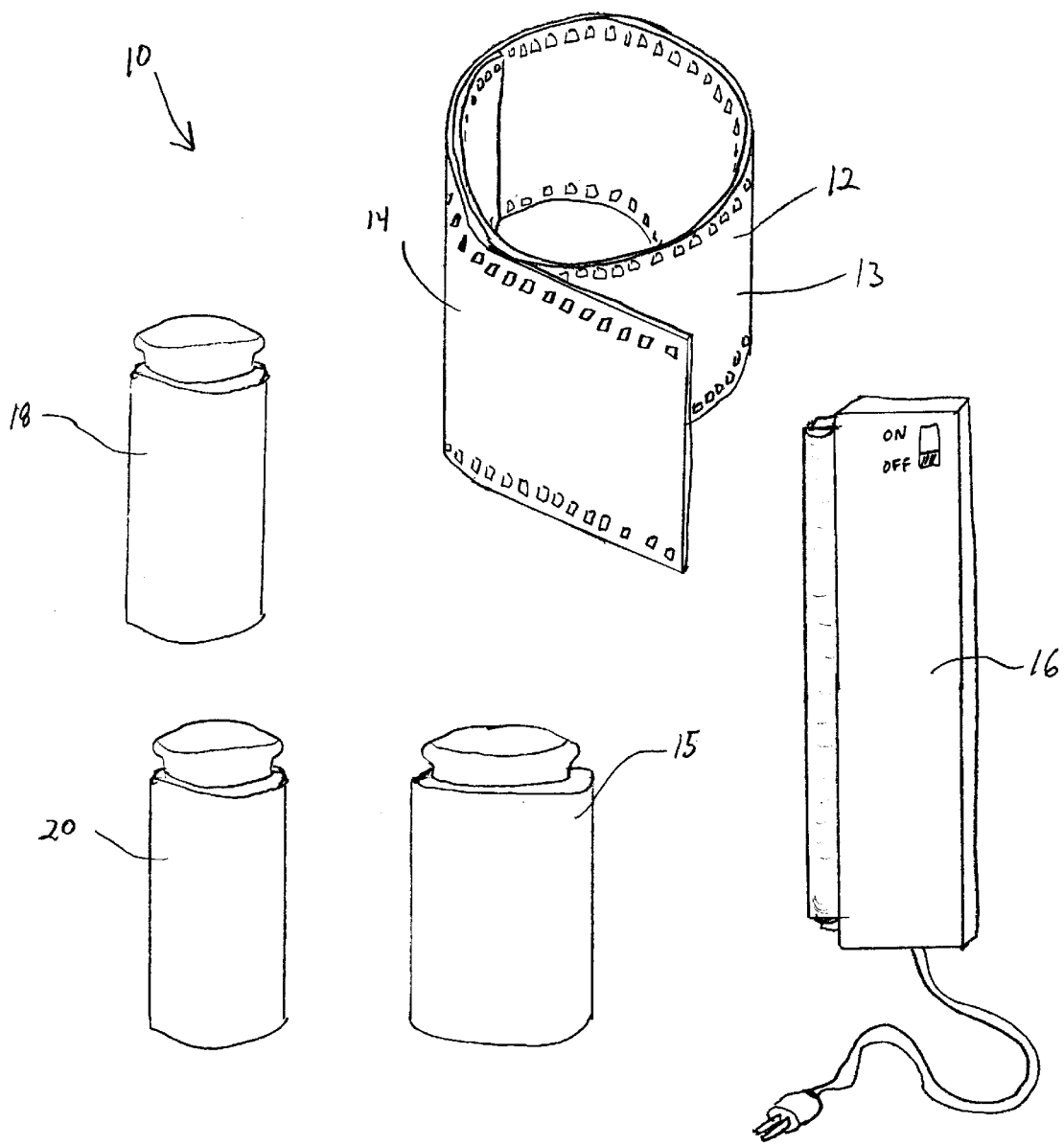
FIG. 1 shows a system in accordance with the invention.

Although certain preferred embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of the preferred embodiment.

Referring to the drawings, a system 10 and method for determining points of abrasion in film equipment are shown. "Abrasion," as used herein, may be any damaging activity to film caused by film equipment such as hindering free passage, scratching, binding, etc.

Figure 2:
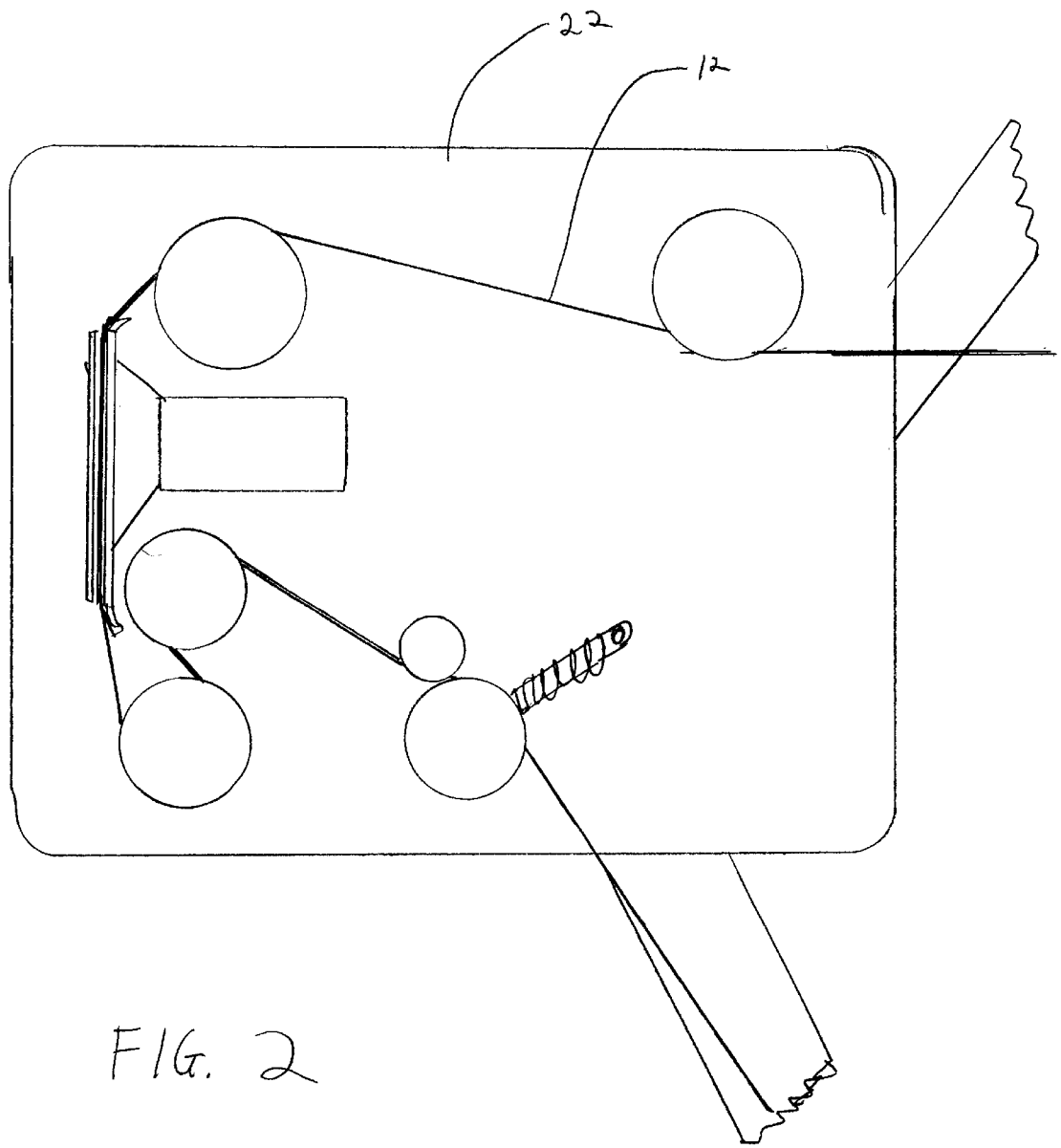
FIG. 2 shows a piece of film equipment under test.

As shown in FIG. 1, system 10 preferably includes a test film 12 having a fluorescent material 14 on an exterior surface thereof and a fluorescence creating light source 16. As an alternative, a section of film 13 and a source of fluorescent material 15 for application to the section of film 13 to create test film 12 may be provided. In addition, a source of removing agent 18 and a source of film cleaner 20, as will be described below, may also be provided. FIG. 2 shows a piece of film equipment 22 having test film 12 running along an operation path thereof.

In accordance with one preferred embodiment of the invention, a user is either provided a test film 12 having fluorescent material 14 on an exterior surface thereof or begins by applying fluorescent material 14 to an exterior surface of a section of film 13 to create test film 12. Film 13/test film 12 is preferably a section of motion picture film of sufficient length to contact at least a part of film equipment 22. For testing of an entire piece of film equipment 22, lengths sufficient to run through the entire operational path of film equipment 22 are preferred, e.g., 100 feet of test film. Further, it is preferable that test film 12 is the same type of film, i.e., size, material, etc., that is normally run in film equipment 22. However, it should be recognized that test film 12 does not necessarily have to be film, but may be any strip-like element that can be contacted to a piece of equipment such that fluorescent material 14 thereon may be deposited on equipment 22.

In one preferred method, fluorescent material 14 is provided or applied only to the emulsion side of test film 12, which aids transfer of fluorescent material 14 to damaging structure of film equipment 22. In this case, because fluorescent material 14 is only on one side, test film 12 may also be provided with a half twist such that part of test film 12 faces one direction and another part faces the opposite direction. In the case of a film projector, this permits a treated side of test film 12 to run through the projector facing both the screen and the lamphouse. In addition, it is preferable for to provide, or have a user include, a leader on test film 12 so the user will not have to thread test film 12 using an active section thereof, which may ruin a test.

Fluorescent material 14 is preferably a fluorescent ink, dye, paint or reactive agent that fluoresces when exposed to a fluorescent creating light source 16 such as an ultraviolet light, e.g., a black light. In accordance with the invention, fluorescent material 14 may be applied to test film 12 in any manner. One preferred manner is for fluorescent material 14 to be brushed or painted onto test film 12. This method finds advantage, for example, when very precise application of fluorescent material 14 to test film 12 is necessary such as when testing of only one side of a structure of film equipment 22 is desired. Of course, any other manner of applying fluorescent material 14 to test film 12 may be used such as dipping, spraying, treating, coating etc.

Next, test film 12 is contacted to at least part of film equipment 22. Where the entire film equipment 22 is being tested, it is preferable to run test film 12 through equipment 22 for some time, e.g., 5 minutes or more, to assure transfer of fluorescent material 14 where appropriate. Furthermore, it is preferable to thread test film 12 exactly as it would be for running an actual film. This makes operator error easier to detect. Those areas of equipment 22 which cause abrasion or otherwise inappropriately contact test film 12 have fluorescent material deposited thereon. Those areas which do not abrade or otherwise inappropriately contact test film 12 do not have fluorescent material 14 deposited thereon.

Next, the part(s) of film equipment 22 under test is illuminated with a fluorescence creating light source 16 to illuminate and fluoresce those areas on film equipment 22 upon which fluorescent material 14 has been deposited. The areas that fluoresce indicate to a user that potentially harmful contact of equipment 22 to test film 12 may be occurring and that remedial action may be necessary to prevent damage to actual film. Illuminating film equipment 22 in a darkened room makes it easier to detect fluorescing parts.

Subsequent to testing, a user may use removing agent 18 to remove fluorescent material 14 from film equipment 22 (potentially using fluorescence creating light source 16 to determine existence of fluorescent material 14) to prevent communication of fluorescent material to actual film. Removing agent 18 may also be used to remove fluorescent material from test film 12 so it can be re-used. In a preferred embodiment, removing agent 18 is an alcohol. However, any other substance capable of removing fluorescent material 14 is suitable. A film cleaner 20 may be provided for general cleaning of test film 12, e.g., to remove access fluorescent material 14. A cleaning tool (not shown) such as a brush may also be provided for applying removing agent 18 and/or film cleaner 20.

As a precursor step to the above-described method, a user may also illuminate part(s) of film equipment 22 to fluoresce any oil, grease, polyester dust, etc., to make sure that previous testing using the invention does not provide a false reading. Prior to actual testing a user should clean any part of film equipment 22 that may give a false reading.

In the example shown in FIG. 2, the film equipment 22 is a motion picture projector. However, film equipment 22 in accordance with this invention may be any machine or apparatus through which a film or tape-like element may be run. In FIG. 2, test film 12 is run along an operation path of film equipment 22. That is, test film 12 is run along a path of film equipment 22 that allows for operation of film equipment 22. This allows the entire piece of film equipment 22 to be tested. It should be recognized, however, that testing in accordance with the invention does not require test film 12 to run an entire operation path of film equipment 22. For instance, a small section of test film 12 may be manually applied to suspected damaging structure of film equipment 22 to test only that structure.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

What is claimed is:

1. A method for determining a source of abrasion in film equipment, the method comprising the steps of:

providing a test film having a fluorescent material thereon;

contacting the test film with at least part of the film equipment; and illuminating at least part of the film equipment with a fluorescence creating light source to fluoresce areas on the film equipment upon which the fluorescent material has been deposited.

2. The method of claim 1, wherein the step of illuminating includes illuminating at least part of the film equipment using an ultraviolet light.

3. The method of claim 1, wherein the step of contacting the test film includes running the test film through an operational path of the film equipment.

4. The method of claim 1, wherein the step of the fluorescent material is one of a fluorescent ink, dye, paint and reactive agent.

5. The method of claim 1, further comprising the step of removing the fluorescent material from the film equipment.

6. The method of claim 1, further comprising the step of illuminating at least part of the film equipment with the fluorescence creating light source to fluoresce areas on the film equipment upon which fluorescent material has been deposited prior to running the test film.

7. A system for determining points of abrasion in film equipment, the system comprising:

a test film having a fluorescent material on an exterior surface thereof; and a fluorescence creating light source for illuminating at least a part of the film equipment subsequent to the test film having been contacted thereto, to determine points of abrasion in the film equipment by fluorescing areas upon which the fluorescent material has been deposited.

8. The system of claim 7, wherein the fluorescence creating light source is an ultraviolet light.

9. The system of claim 7, wherein the test film is run through an operational path of the film equipment.

10. The system of claim 7, wherein the fluorescent material is one of a fluorescent ink, dye, paint and reactive agent.

11. The system of claim 7, wherein the fluorescent material is brushed on the test film.

12. The system of claim 7, further comprising a removing agent for removing the fluorescent material from the film equipment.

13. The system of claim 12, wherein the removing agent is an alcohol.

14. The system of claim 7, further comprising a film cleaner for cleaning the test film.

15. A system for determining points of abrasion in film equipment, the system comprising:
- a section of film for contacting at least a part of the film equipment;
- a source of fluorescent material for application to the section of film to create a test film; and
- a fluorescence creating light source for fluorescing any part of the film equipment having fluorescent material deposited thereon from the test film having contacted the part.

16. The system of claim 15, wherein the fluorescence creating light source is an ultraviolet light.

17. The system of claim 15, wherein the test film is run through an operational path of the film equipment.

18. The system of claim 15, wherein the fluorescent material is one of a fluorescent ink, dye, paint and reactive agent.

19. The system of claim 15, further comprising a removing agent for removing the fluorescent material from the film equipment.

20. The system of claim 19, wherein the removing agent is an alcohol.

21. The system of claim 15, further comprising a film cleaner for cleaning the section of film.

* * * * *